United States Patent
Fiess et al.

(10) Patent No.: US 11,868,522 B2
(45) Date of Patent: Jan. 9, 2024

(54) METHOD FOR ASCERTAINING A VIEWING DIRECTION OF AN EYE

(71) Applicant: Robert Bosch GmbH, Stuttgart (DE)

(72) Inventors: Reinhold Fiess, Durbach (DE); Andreas Petersen, Marbach (DE); Thomas Alexander Schlebusch, Renningen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 548 days.

(21) Appl. No.: 17/259,157

(22) PCT Filed: Aug. 12, 2019

(86) PCT No.: PCT/EP2019/071562
§ 371 (c)(1),
(2) Date: Jan. 8, 2021

(87) PCT Pub. No.: WO2020/043472
PCT Pub. Date: Mar. 5, 2020

(65) Prior Publication Data
US 2021/0271320 A1      Sep. 2, 2021

(30) Foreign Application Priority Data
Aug. 29, 2018   (DE) .......................... 102018214637.3

(51) Int. Cl.
*G02B 5/32* (2006.01)
*G06F 3/01* (2006.01)
*G02B 27/00* (2006.01)

(52) U.S. Cl.
CPC ......... *G06F 3/013* (2013.01); *G02B 27/0093* (2013.01); *G02B 5/32* (2013.01)

(58) Field of Classification Search
CPC .................. G02B 5/32; G02B 27/0093; G02B 2027/0178; G06F 3/013; H04N 13/383; G01C 21/365; G06T 19/006
See application file for complete search history.

(56) References Cited

U.S. PATENT DOCUMENTS 7,657,062 B2   2/2010   Pilu
9,529,191 B2   12/2016  Sverdrup et al.
(Continued)

FOREIGN PATENT DOCUMENTS

CN   102802502 A   11/2012
CN   104434022 A   3/2015
(Continued)

OTHER PUBLICATIONS

Giorgio Capelli, "Laser velocimeter for the measurement of eye movements", 2011 (Year: 2011).*
(Continued)

*Primary Examiner* — Maurice C Smith
(74) *Attorney, Agent, or Firm* — NORTON ROSE FULBRIGHT US LLP; Gerard A. Messina

(57) ABSTRACT

A method for ascertaining a viewing direction of an eye. A laser beam emitted by a laser source is passed over at least two scanning points on the eye, using a reflection element and a deflecting element. A self-mixing effect of the scanning laser beam reflected by the eye into the laser source is used, in order to determine, for the at least two scanning points, the optical path length from the laser source to the at least two scanning points on the surface of the eye and/or a reflectivity of the eye at the at least two scanning points.

13 Claims, 7 Drawing Sheets

(56) References Cited

U.S. PATENT DOCUMENTS

| | | | |
|---|---|---|---|
| 2016/0349515 A1 | 12/2016 | Alexander et al. | |
| 2017/0115483 A1 | 4/2017 | Aleem et al. | |
| 2018/0129041 A1 | 5/2018 | Aleem et al. | |
| 2019/0187482 A1* | 6/2019 | Lanman | G02B 27/0179 |
| 2020/0043391 A1* | 2/2020 | Maimone | G02B 27/0093 |

FOREIGN PATENT DOCUMENTS

| | | | | |
|---|---|---|---|---|
| CN | 105072978 A | | 11/2015 | |
| CN | 105783802 A | * | 7/2016 | G01B 17/04 |
| CN | 106663183 A | | 5/2017 | |
| CN | 107515466 A | | 12/2017 | |
| CN | 107710048 A | | 2/2018 | |
| CN | 108027516 A | | 5/2018 | |
| DE | 102016201567 A1 | | 8/2017 | |
| DE | 102016226294 A1 | | 7/2018 | |
| EP | 1840627 A2 | | 10/2007 | |
| EP | 3422147 A1 | * | 1/2019 | G02B 27/017 |
| WO | WO-2016009334 A1 | * | 1/2016 | A61B 3/165 |

OTHER PUBLICATIONS

International Search Report for PCT/EP2019/071562, dated Nov. 11, 2019.

Taimre, Thomas et al., "Laser Feedback Interferometry: A Tutorial on the Self-Mixing Effect for Coherent Sensing," vol. 7, No. 3, 2015, pp. 570-631. <https://www.osapublishing.org/DirectPDFAccess/142F68D6-B12C-36F3-B1528BDFABA52008_324452/aop-7-3-570.pdf?da=1&id=324452&seq=0&mobile=no> Downloaded Jan. 4, 2021.

English abstract of DE50112749D1 [a copy of the document is not available.].

Zhang, Weilian: "Orthogonally Polarized Laser Devices and the Development of Applications Thereof," Proceedings of the 2004 National Optoelectronics Technology Academic Exchange Meeting, China, pp. 289-298; abstract and p. 293—with English translation.

Dongmei and Ming:"A Sine-phase Modulating Semiconductor Laser Self-mixing Interference Micro-displacement Measurement System," Proceedings of the Photonics Innovation and Industrialization—Yangtse Delta Photonics Innovation Forum and 2006 Anhui PhD Science & Technology Forum, Abstract only, with English translation.

* cited by examiner

METHOD FOR ASCERTAINING A VIEWING DIRECTION OF AN EYE

FIELD

The present invention relates to a method for ascertaining a viewing direction of an eye, a projection device for a pair of smart glasses, a pair of smart glasses, a computer program, a machine-readable storage medium, as well as an electronic control unit.

BACKGROUND INFORMATION

The object of oculography, eye monitoring, or also eye tracking is to monitor the movement of the eyes and to ascertain the viewing direction. The technology is widely applied in consumer research, e.g., in the monitoring of the reader's flow, in order to optimize the placement of advertising.

In smart glasses, such as, e.g., helmet-mounted and/or head-mounted displays (HMD) or head-worn displays (HWD), the technology is also used for adapting the displayed picture content as a function of the viewing direction of the user. On one hand, for example, in order to reduce electrical power output, the display of high-resolution picture content may be limited to the range of sharpest vision, and lower resolution content may be displayed peripherally. On the other hand, primarily in the case of augmented reality systems, which are partially or fully transparent systems that combine natural perception of the surroundings with the display of virtual content, information, supplements and instructions may be made visible only for viewed objects for reasons of clarity.

The available systems may be subdivided technologically into the following categories:

Camera-based systems: A camera is pointed from the eyeglass frame to the eye. Some systems additionally include one or more infrared light sources, which are optionally operated in a modulated manner. The viewing direction is ascertained from the image data, using an eye model, contrast-based detection of the pupil (dark vs. bright pupil), limbus tracking (contrast boundary between the cornea and sclera), or localization of the corneal reflex. Systems have also been described, which project a pattern (mostly point-cloud or linear pattern) onto the eye, using structured light, and ascertain the viewing direction via the characteristic change of shape in the region of the cornea in comparison with the region of the sclera.

Scanning laser systems: A laser source integrated in the eyeglass frame is guided over the eye, for example, by a microelectromechanical (MEMS) micromirror. Conventional methods ascertain the viewing direction on the basis of the corneal reflex.

Electrical measurement: The measurable electric fields resulting from ion displacement during muscle contraction may be recorded as a so-called electromyogram. If the method is used in the region of the eyes, it is referred to as an electrooculogram. Using signal processing of the derived electrical signals, eye movement may be deduced, as well.

Electromagnetic measurement: If a coil is situated in the magnetic field of another coil, the magnetic coupling of the two coils is a function of their orientation with respect to each other. If one coil is integrated in the eyeglass frame and another coil is integrated in a contact lens, a determination of the viewing direction is possible, as well.

SUMMARY

In accordance with an example embodiment of the present invention, a method is used for ascertaining a viewing direction of an eye. This relates to, in particular, an eye of a user of smart glasses. A pair of smart glasses may be understood as an HMD. The term smart glasses is also to be understood as video glasses, a helmet display, or a VR helmet.

In this connection, the viewing direction of the user is given by a receiving point, which may be, e.g., the center of the pupil, and by a directional vector, along which the eye sees, and which may be given, e.g., by a vector through the center of the pupil and a point on the retina, e.g., the macula. The receiving point may change, e.g., due to displacement of the glasses relative to the eye.

In the example method, a laser beam emitted by a laser source is passed over at least two scanning points on the eye, that is, on the surface of the eye, using a reflection element and a deflecting element.

The reflection element is used for reflecting the light beam onto the deflecting element. A reflection element may be understood, for example, as a mirror, in particular, a micromirror or an array of micromirrors, or a hologram. An optical path of the light beam may be adapted to given spatial conditions with the aid of the reflection element. For example, the reflection element may be implemented as a micromirror. The micromirror may be formed to be movable, for instance, to include a reflecting surface tiltable about at least one axis. Such a reflection element provides the advantage of a particularly compact type of construction. It is also advantageous if the reflection element is configured to change an angle of incidence and, additionally or alternatively, a point of incidence of the light beam on the deflecting element. In this manner, the deflecting element may be scanned two-dimensionally by the beam, in particular, in rows and columns, for instance.

The deflecting element may be a holographic element or a freeform mirror.

A holographic element may be understood, for example, as a holographic optical element, abbreviated as HOE, which may carry out the function of, for example, a lens, a mirror or a prism. Depending on the specific embodiment, the holographic element may be selective for particular wavelengths (colors of light) and angles of incidence.

Available photosensitive materials (e.g., photopolymer films) for producing holographic elements may only be irradiated in the visible wavelength range. However, the use of holographic elements in the near-infrared range would be highly advantageous for the method, in order that the measuring method is not visible to the user, and in order not to interfere with, e.g., the display of information of a pair of smart glasses, due to this. Using appropriate measures, such as angular derivative action and/or optical immersion accessories, the photosensitive material having suitable functionality in the visible wavelength range may be irradiated in such a manner, that in the case of use in the near infrared, the holographic element has the desired optical target functionality.

Holographic elements may be manufactured in large quantities, in particular, using optical copying methods. If the holographic element fulfills optical functions, which may be irradiated in the photosensitive material using simple point or collimated light sources, the copying method (manufacturing method) turns out to be considerably simpler. In this manner, the holographic element may be manufactured highly cost-effectively.

The holographic element may be transparent. In this manner, image information may be superimposed on the surroundings on the eyeglass lens.

In the method, a laser beam emitted by a laser source is passed over at least two scanning points on the eye, using a reflection element and a deflecting element.

The laser beam is preferably passed over a plurality of scanning points. In this connection, the scanning points are distributed over the surface of the eye in such a manner, that the viewing direction of the eye may be ascertained. This is then preferably the case, if the scanning points on the upper surface of the eye cover at least a part of the pupil. It is further preferable for the scanning points on the surface of the eye to cover the entire eye. In this case, the word "cover" is not understood to mean that each individual point must be scanned. It is sufficient for the contour of the scanned points to be larger than the part of the eye or the entire eye.

In the example method, a self-mixing effect of the scanning laser beam reflected back into the laser source by the eye is used, in order to determine, for the at least two scanning points, the optical path length from the laser source to the at least two scanning points on the surface of the eye and/or a reflectivity of the eye at the at least two scanning points.

In the self-mixing effect, also called laser self-mixing, the coherent beam emitted by a laser is scattered by a surface, and a portion of this beam arrives back again in the laser cavity, the optical resonator. If twice the distance to the scatterer corresponds to an integral multiple of the wavelength, then the radiation scattered back is in phase with the beam in the laser cavity. Consequently, it adds constructively to the beam located there, reduces the laser threshold, and therefore increases the power output of the laser. If the distance of the scatterer and, therefore, the optical path length traveled, are now changed, positive or negative interference occurs again and again inside the laser cavity as a function of the distance, which means that the power of the laser is modulated in a sinusoidal pattern between a beam maximum and a beam minimum. Similar instances of intensity modulation are attained, when the wavelength of the laser is modulated, or when the frequency of the backscattered laser light changes, e.g., due to the Doppler effect, which occurs in response to reflection by moving objects. If the optical radiant power is now measured by a photodiode (monitoring photodiode), the change in intensity of the backscattered laser power may be deduced from the change in amplitude of the radiant power. By analyzing the number of oscillations, e.g., by counting the zero crossings or the maximum values, the number of oscillations, that is, zero crossings, of constructive and destructive interference may also be deduced, and therefore, in the case of a known laser wavelength and modulation, the distance and any changes in distance between the laser cavity and the scatterer, as well as the velocity component of the scatterer parallel to the laser beam, may be deduced. In addition to the distance and velocity of the scatterer, the absolute intensity of the backscatter signal may be used to calculate the reflectivity of the scatterer. Accordingly, the laser preferably includes an integrated photodiode, which measures the optical radiant power of the laser.

According to one preferred specific embodiment of the present invention, the viewing direction of the eye is ascertained on the basis of different reflectivities of different parts of the eye at the at least two scanning points. This specific embodiment is presently referred to as implementation variant 1.

The different parts of the eye are preferably the sclera, iris and the pupil. Based on the different reflectivities of the sclera, iris and pupil, which are obtained from the scan over the eye, the viewing direction of the eye may be ascertained in an advantageous manner.

According to one preferred specific embodiment of the present invention, the viewing direction of an eye is ascertained, using the "red-eye effect," by searching for a scanning point on the eye, at which the laser beam is reflected by the retina of the eye. This specific embodiment is presently referred to as implementation variant 1b.

In the case of the conventional "red-eye effect," a reflection occurs on the retina. If the light source is situated approximately on the optical axis of the observer, then the angles of incidence and reflection of the beam are equal, and a marked reflection is observable. For all other angles, the pupil appears dark, since the angles of incidence and reflection of the beam do not match, and the radiant power is absorbed due to multiple reflections in the eye.

This feature advantageously allows an exact determination of the pupil position, since the reflectivity of the pupil, that is, of the retina visible behind it, differs sharply from the reflectivity of other parts of the eye.

According to one preferred specific embodiment of the present invention, a surface profile of the eye is ascertained, in that with the aid of the self-mixing effect, which causes modulation of the laser power while the laser beam is passed over the eye, a change in an optical path length from the laser source to a current scanning point on the surface of the eye is ascertained. This specific embodiment is presently referred to as implementation variant 2.

The modulation of the laser power is a sinusoidal function of the change in the optical path length from the laser source to the current scanning point on the surface of the eye. Thus, the change in the optical path length may be ascertained in light of the measured modulation.

From this, it follows that in light of the known geometric configuration of the laser source, the reflection element and the deflecting element, as well as in light of the known optical characteristics of the deflecting element, the distance from the laser source to the surface of the eye may be ascertained for each scanning point. Since the geometric configuration of the laser source, the reflection element and the deflecting element are known, then, consequently, the surface profile of the eye may also be ascertained, through which, in turn, the viewing direction may be ascertained.

A change in the optical path length results in the passing-through of a plurality of extreme points in the laser power modulation, due to constructive and destructive interference of the self-mixing effect. The relative change in shape may be determined by analysis of the number of extrema passed through.

Since the wavelength of the utilized laser beam is preferably in the near infrared and, therefore, on the order of one micrometer, a change in the surface profile of the eye by, e.g., 1 mm causes more than 2000 extreme points to be passed through.

This shows that using this technique, the surface profile of the eye may be measured highly accurately. As an alternative to the feature mentioned above, a gradient of the modulation of the laser power may be used for determining a gradient of the surface profile of the eye. In other words, an increase in the change in distance may be connected to a time interval of the extrema or zero crossings of the optical laser power. Thus, the frequency of the time-related extrema may also be utilized as a measure of the shape and, therefore, of the viewing direction.

According to one preferred specific embodiment of the present invention, the specific embodiment, according to which different reflectivities of different parts of the eye are ascertained, and the specific embodiment, according to which a change in the optical path length is ascertained, may be combined with each other. This has the advantage that the surface profile of the eye may be determined considerably more accurately.

According to a further preferred specific embodiment of the present invention, the deflecting element is positioned and configured in such a manner, that for each scanning position of the reflection element, the laser beam is deflected by the deflecting element in, in each instance, the same direction. This direction is preferably parallel to at least one viewing direction of the eye and, particularly preferably, parallel to a viewing direction straight ahead to the front. The viewing direction straight ahead to the front is defined, such that the viewing direction points substantially orthogonally on the plane of the eyeglass lens.

This specific embodiment of the HOE is preferred for implementation variant 1 and implementation principle 2.

In this connection, the laser beams that are incident as a function of the scanning angle are deflected to form laser beams emerging in parallel. Since the orientation of the deflecting element and the reflection element is fixed by the eyeglass frame, consequently, the position of emergence of the laser beam from the deflecting element in the direction of the eye is also fixed. Consequently, the need for a further coordinate system transformation as a function of the distance of the eye from the deflecting element is advantageously eliminated.

According to another further preferred specific embodiment, the deflecting element is positioned and configured in such a manner, that for each scanning position of the reflection element, there is an eye position, whose viewing direction is parallel to the propagation direction of the laser beam deflected by the deflecting element in this scanning position. In this case, the laser beams coming from the deflecting element are preferably convergent and intersect at a point in the interior of the eyeball, preferably at the point of rotation of the eye.

Through this, a laser beam, which runs parallelly to the visual axis, is advantageously present for each viewing angle of the eye at the position, at which the eye meets the deflecting element. In addition, an increase in the resolution is obtained by limiting the angular range.

According to a further preferred specific embodiment of the present invention, the deflecting element is positioned and configured in such a manner, that the laser beams, which are deflected by the deflecting element for different scanning positions of the reflection element, are divergent. In this connection, the beams are preferably divergent and intersect at a point, which lies on a point of the viewing direction, preferably, a viewing direction straight ahead to the front.

This specific embodiment of the present invention is preferred primarily for implementation variants 1 and 2. If the surface of the deflecting element is smaller than the entire eye region, this implementation advantageously enables an expansion of the measuring range, e.g., in order to utilize skin regions about the eye, as well, for calibrating a reference coordinate system. The field of view is defined to be the angular range, which may be seen from the eye. The eye region is defined as a surface, in which the eye may be situated.

According to a preferred specific embodiment of the present invention, the deflecting element is positioned and configured in such a manner, that the deflecting element has at least two different regions; in each instance, each region of the deflecting element deflects the laser beams, which strike it, onto a point on the eye.

The different regions are preferably disjoint.

The deflecting element preferably has a plurality of regions; the points deflected from the plurality of regions onto the eye being distributed uniformly over the eye. According to a further preferred specific embodiment, such a region is a horizontally-running row or scanning row of the deflecting element that is preferably situated on the eyeglass lens. It is even further preferable for the deflecting element to include a plurality of rectilinear regions running horizontally; in each instance, each rectilinear region or a plurality of rectilinear regions deflecting the laser beams striking them onto a point on the eye. In this case, there is a one-to-one association between the horizontal regions and the scanning points on the eye; each region being assigned to only one point, and each point being assigned to only one region.

This specific embodiment is advantageous, if the measuring quality in a rapidly scanning system is not sufficient, or if, in other words, the light output per measuring point is overly low.

The at least two different regions are defined analogously to the eyebox concept of an HOE; the regions focusing the beams onto a point of the eye, the so-called eyebox, in a manner similar to a parabolic mirror. This advantageously allows the evaluation electronics to ascertain a mean value longer over the received signal, above all, in implementation variant 1, which means that the signal-to-noise ratio is improved.

In a high-resolution projection system having, for example, 720 rows, sufficient measuring points are produced for measuring the viewing angle with a comparatively long residence time at a measuring point.

The projection device for a pair of smart glasses includes a laser source for emitting a light beam. In addition, the projection device includes a deflecting element positioned or positionable on an eyeglass lens of the smart glasses, for deflecting the laser beam in the direction of an eye of the user and/or for focusing the laser beam. Furthermore, the projection device includes a reflection element for reflecting the laser beam onto the deflection element.

The projection device is constructed and configured to carry out a method for ascertaining a viewing direction of an eye. Consequently, the projection device may attain the same advantages as the method described above.

The smart glasses include an eyeglass lens and a projection device described above; the deflecting element being situated on the eyeglass lens. The smart glasses achieve, just as the projection device, the same advantages as the method described above.

The present invention further includes a computer program, which is set up for executing the described steps of the method, in order to be able to perform the above-described method, using this computer program. In addition, the present invention includes a machine-readable storage medium, in which such a computer program is stored, as well as an electronic control unit, which is configured to carry out the steps of the described method. Such an electronic control unit may be integrated into a projection device or smart glasses, for example, in the form of a microcontroller.

BRIEF DESCRIPTION OF THE DRAWINGS

Exemplary embodiments of the present invention are depicted in the figures and explained in greater detail in the following description.

DETAILED DESCRIPTION OF EXAMPLE EMBODIMENTS

Figure 1:
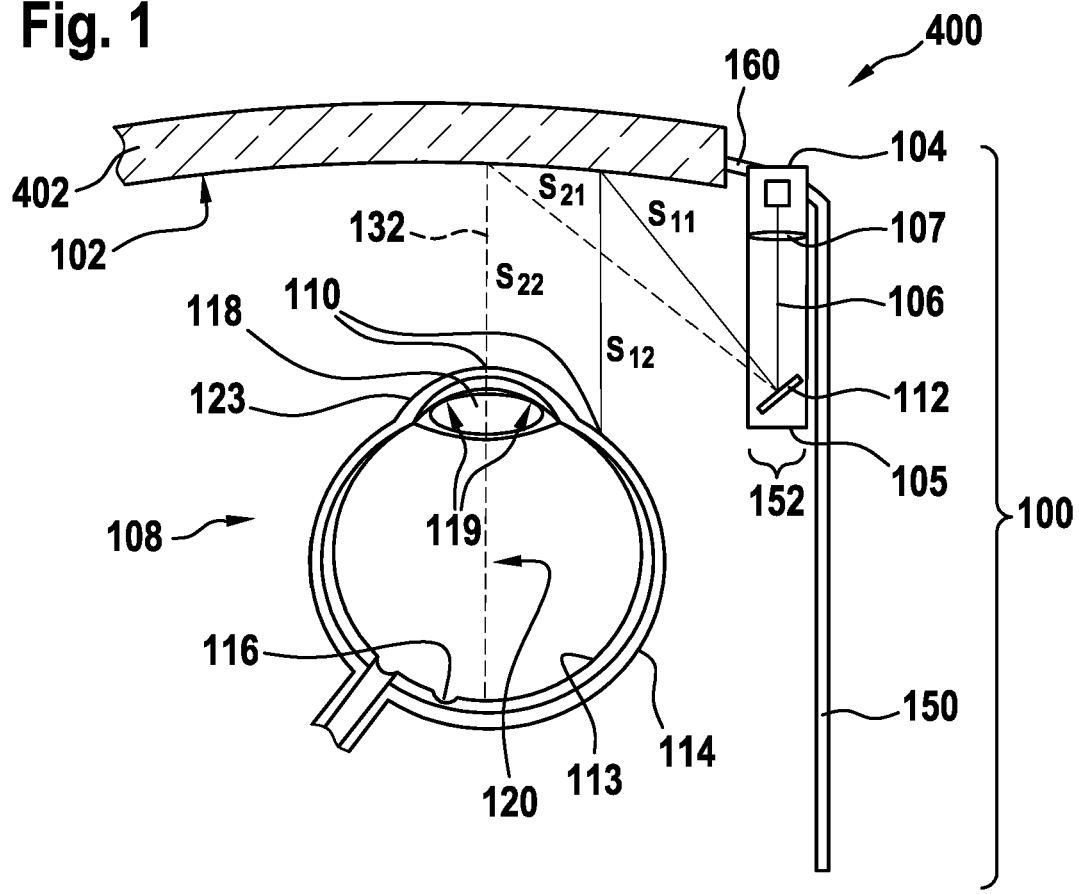
FIG. 1 shows a schematic representation of a set-up of a pair of smart glasses according to a specific embodiment of the present invention, as well as of an eye of a user.

FIG. 1 shows the basic method of functioning of smart glasses 400, in particular, in light of implementation variant 1. Smart glasses 400 include an eyeglass lens 402 and a projection device 100. Projection device 100 includes scanning optics 152 and a deflecting element 102, which, in this specific embodiment, is constructed as a holographic element (HOE). Deflecting element 102 is attached to eyeglass lens 402. Scanner optics 152 are situated in a housing 105 and include a laser source 104, a collimation element 107, a reflection element 112, as well as an element for beam shaping and/or collimation, which is not illustrated and is positioned after reflection element 112.

A light beam 106 emitted by scanner optics 152 is transmitted through an outlet window in the direction of deflecting element 102. The light beam 106 deflected by deflecting element 102 then strikes an eye 108 of a user. Scanner optics 152 are situated in a housing 105 attached to eyeglass frame 160 and to temple 150.

Projection device 100 may carry out a method for ascertaining a viewing direction of an eye.

In a further specific embodiment of the present invention, the projection device may simultaneously carry out a method for generating a visible image on the retina and a method for ascertaining a viewing direction of the eye. In this context, the optical functions of the HOE in the deflecting element may differ for different wavelengths.

FIG. 1 shows two exemplary optical paths, a first optical path 131, on which laser beam 106 strikes eye 108 in the region of sclera 114, and which has a first reflectivity, as well as a second optical path 132, on which laser beam 106 strikes eye 108 in the region of cornea 123, and which has a second reflectivity. First optical path 131 corresponds to a first mirror position of reflection element 112, at which the distance from reflection element 112 to deflecting element 102 is designated by reference character $s_{11}$ and the distance from deflecting element 102 to the surface of eye 108, in this case, to scanning point 110 on sclera 114, is designated by reference character $s_{12}$. Second optical path 132 corresponds to a second mirror position of reflection element 112, at which the distance from reflection element 112 to deflecting element 102 is designated by reference character $s_{21}$ and the distance from deflecting element 102 to the surface of eye 108, in this case, to scanning point 110 on cornea 123, is designated by reference character $s_{22}$. In the illustration of FIG. 1, in the second mirror position of reflection element 112, laser beam 106 strikes eye 108 along viewing direction 120, so that laser beam 106 initially strikes cornea 123 and then retina 113.

Figure 2:
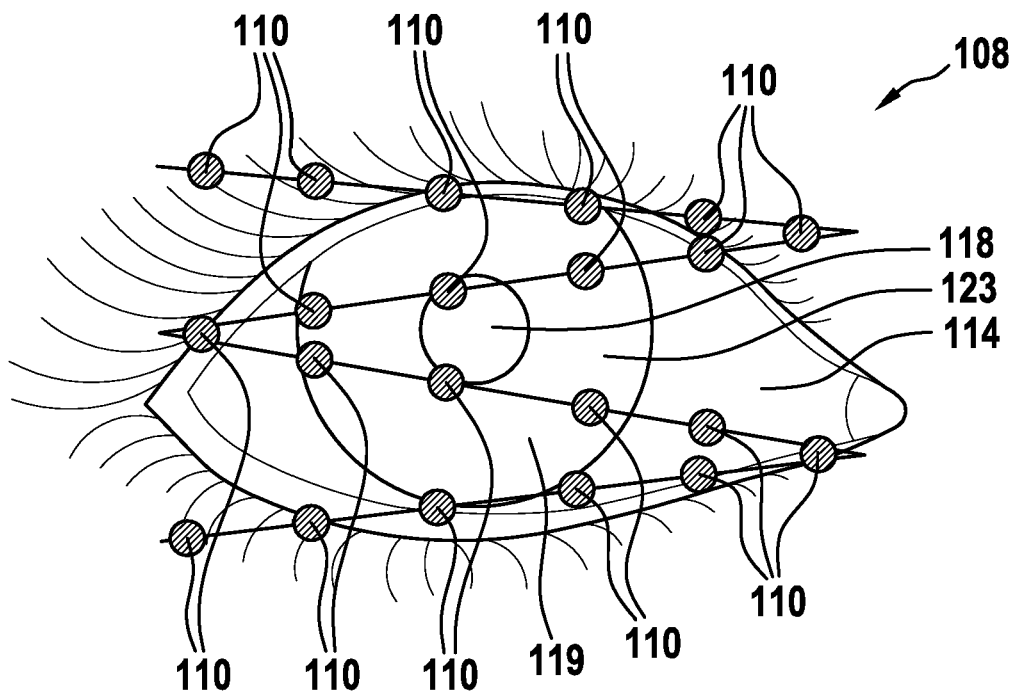
FIG. 2 shows a schematic distribution of scanning points on a scanned eye in accordance with a specific embodiment of the method of the present invention.

During the scanning of laser beam 106, it is moved in a zigzag pattern over the eyeball in a manner comparable to the scanning of earlier picture tubes, that is, at a rapid row frequency and lower column frequency, as FIG. 2 shows in a simplified manner. In a real system, e.g., 1280 scanning points 110 per row and 720 rows are used.

Figure 3:
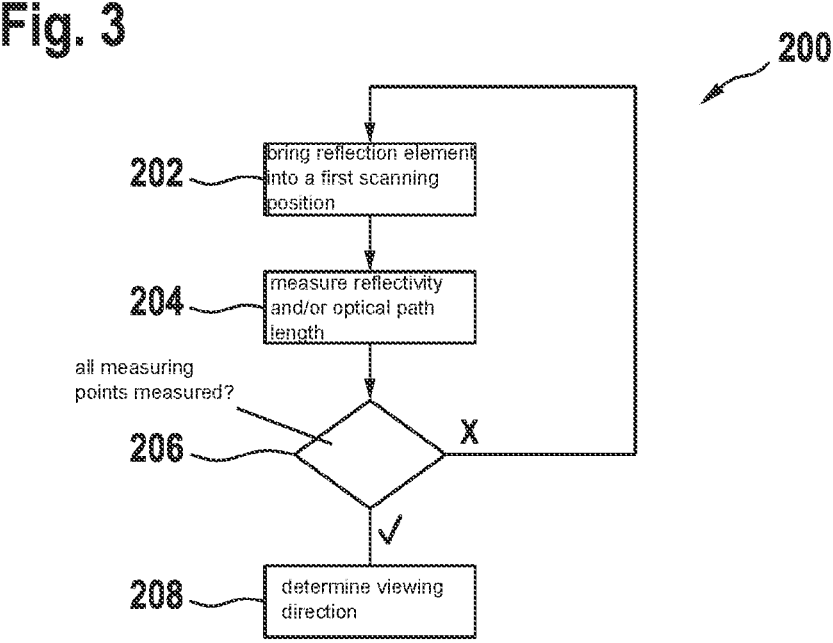
FIG. 3 shows a schematic flow chart of a method according to one exemplary embodiment of the present invention.

FIG. 3 shows a method 200 for ascertaining the viewing direction 120 of eye 108. Method 200 starts in step 202, in that reflection element 112 is brought into a first scanning position, in which laser beam 106 strikes a first scanning point 110 on the surface of eye 108. In the next step 204, depending on the specific embodiment of method 200, either a reflectivity, the optical path length from laser source 104 to the current scanning point 110 on the surface of the eye, or both, are measured. For this, different types of HOE's are suitable as deflecting elements 102, depending on the specific embodiment of method 200. In next step 206, an inquiry is made as to whether or not all measuring points 110 have been measured. If all measuring points 110 have already been measured, then the method continues with step 208, in which viewing direction 120 is determined in light of the measured measuring points 110. If all measuring points 110 have not yet been measured, then the method continues with step 202, in which the next scanning point is now set at reflection element 112. In this connection, a check stands for a yes to the inquiry, an x stands for a negative answer to the inquiry.

The determination of viewing direction 120 also differs in the respective methods of implementation variants 1, 1b and 2.

Figure 4:
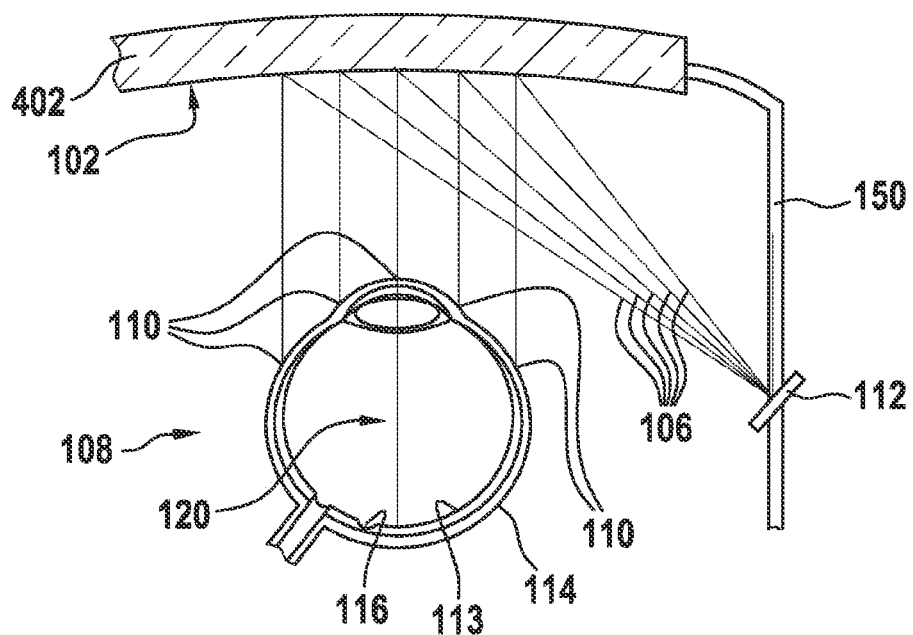
FIGS. 4, 5, 6, 7, 8, and 9 each show a schematic representation of a set-up of a pair of smart glasses according to a specific embodiment, as well as of an eye of a user; the physical characteristics of the deflecting element, which is constructed as an HOE, differ.

FIG. 4 shows a pair of smart glasses 400, as well as eye 108, which is in the same position as in FIG. 1. However, in the specific embodiment of FIG. 4, the HOE of deflecting element 102 is constructed in such a manner, that laser beams 106 are each reflected parallelly by deflecting element 102. In this case, laser beams 106 are each parallel to temple 150. The direction of laser beam 106 corresponds to viewing direction 120 of eye 108, as well, which is illustrated in FIG. 4.

In this constellation, a method 200, in which a reflectivity is determined for each scanning point 110 on the surface of the eye, is preferably carried out. This is particularly advantageous for implementation variants 1 and 2.

Figure 5:
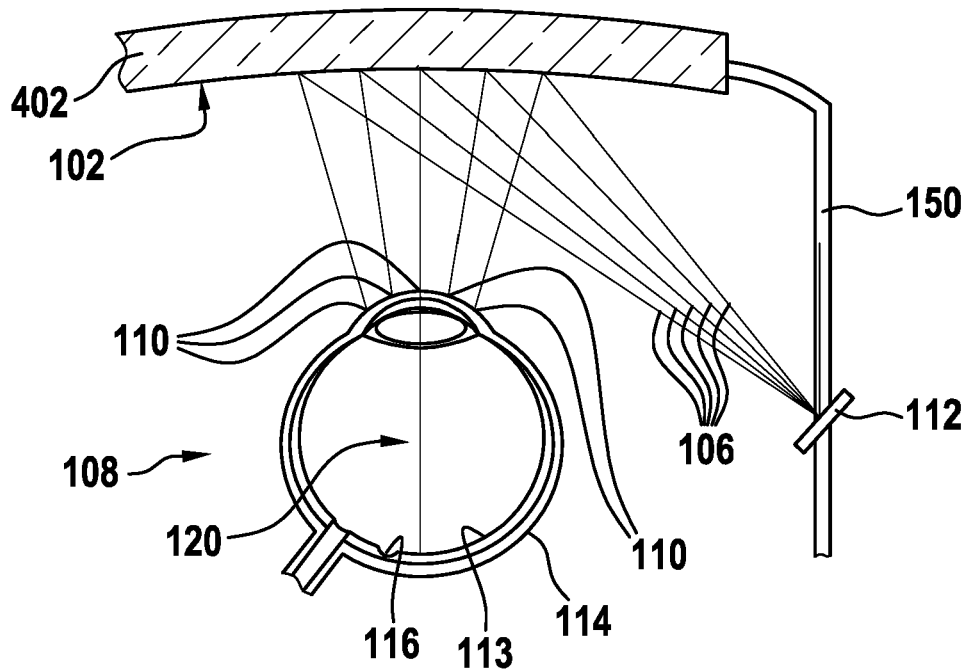

Just as in FIG. 4, FIG. 5 shows a pair of smart glasses 400, as well as eye 108. However, in contrast to the specific embodiment of FIG. 4, the HOE of deflecting element 102 of FIG. 5 is constructed in such a manner, that laser beams 106 are reflected by deflecting element 102 in a convergent manner. This is particularly advantageous for implementation variant 1b and an increase in the spatial resolution of the measurement.

Figure 6:
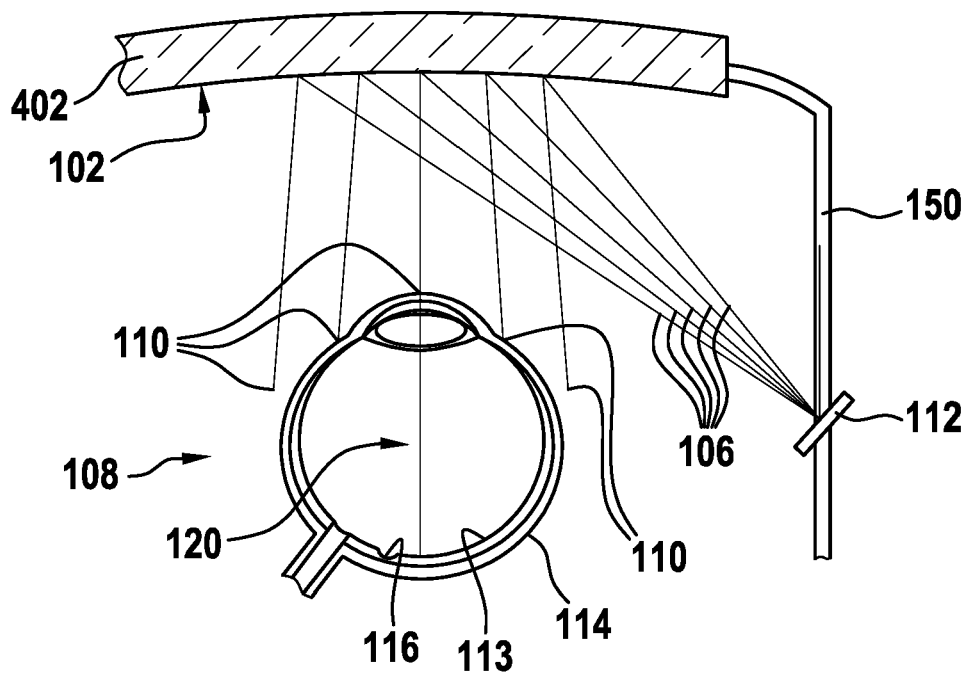

Just as in FIGS. 4 and 5, FIG. 6 shows a pair of smart glasses 400, as well as eye 108. However, in contrast to the specific embodiment of FIGS. 4 and 5, the HOE of deflecting element 102 of FIG. 6 is constructed in such a manner, that laser beams 106 are reflected by deflecting element 102 in a divergent manner. If the surface of the HOE is smaller than the entire eye region, this implementation enables an expansion of the measuring range, e.g., in order to utilize skin regions about the eye, as well, for calibrating a reference coordinate system.

This is particularly advantageous for implementation variants 1 and 2.

Figure 7:
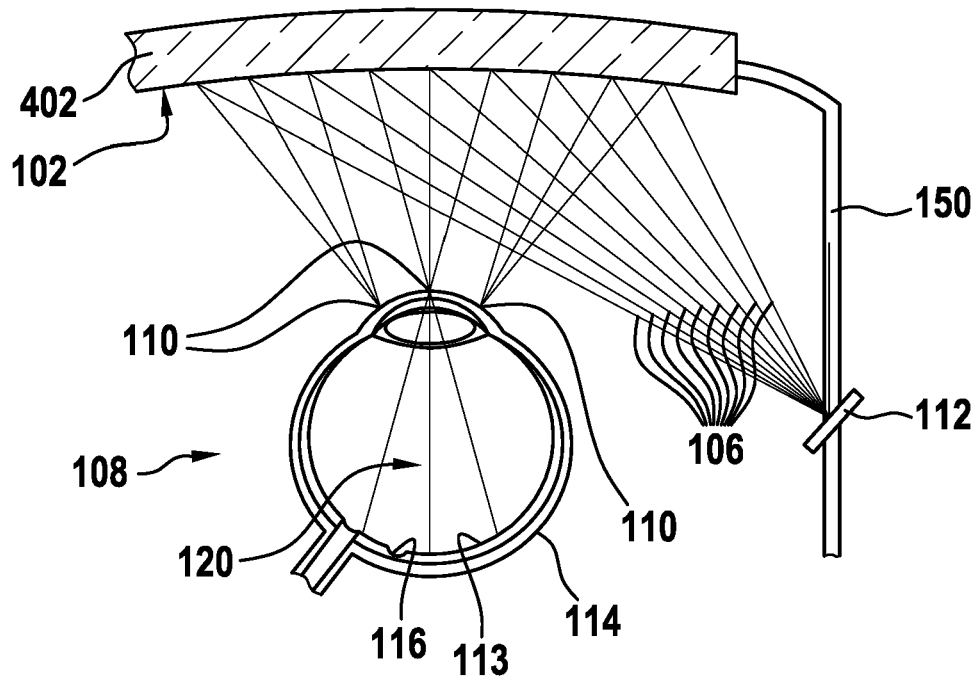

Just as in FIGS. 4, 5 and 6, FIG. 7 shows a pair of smart glasses 400, as well as eye 108. However, in contrast to the specific embodiments of FIGS. 4, 5 and 6, the HOE of deflection element 102 of FIG. 7 is constructed in such a manner, that a plurality of eyeboxes are present, which focus the beams, in each instance, on a scanning point 110 of the eye in a manner similar to a parabolic mirror.

In particular, this is then advantageous, if the measuring quality in a rapidly scanning system is not sufficient. This advantageously allows the evaluation electronics to ascertain a mean value longer over the received signal, above all, in the case of implementation principle 1, and thus, to improve the signal-to-noise ratio.

Figure 8:
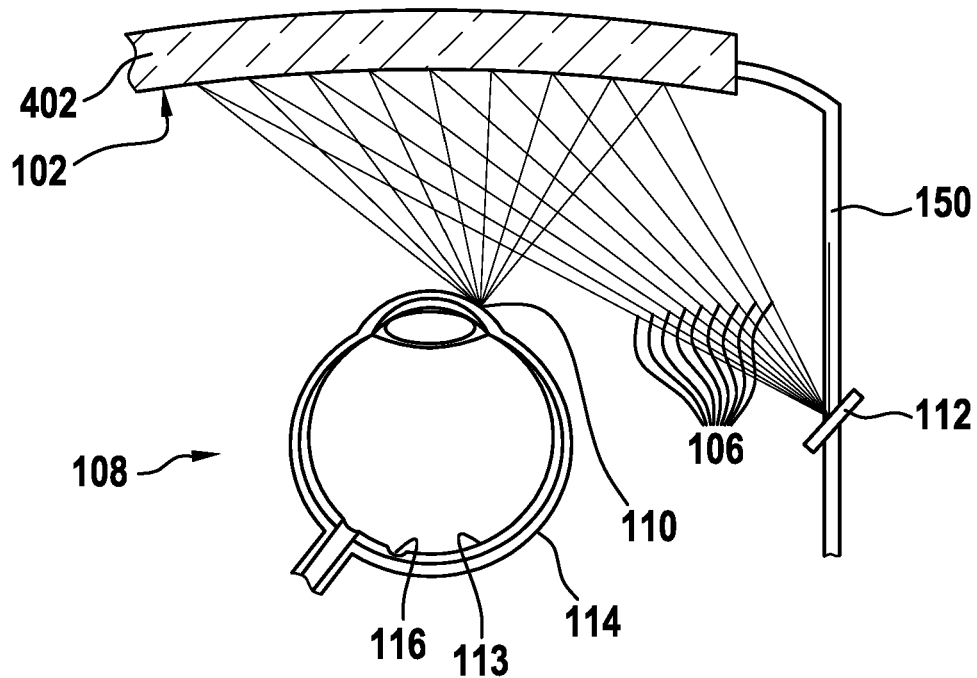
Figure 9:
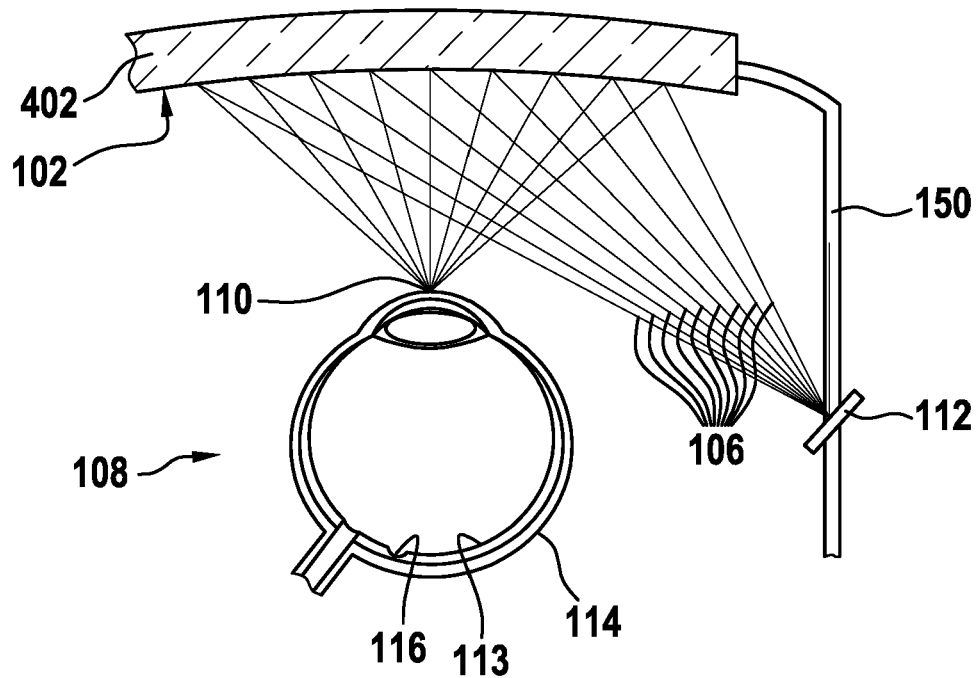
Figure 10:
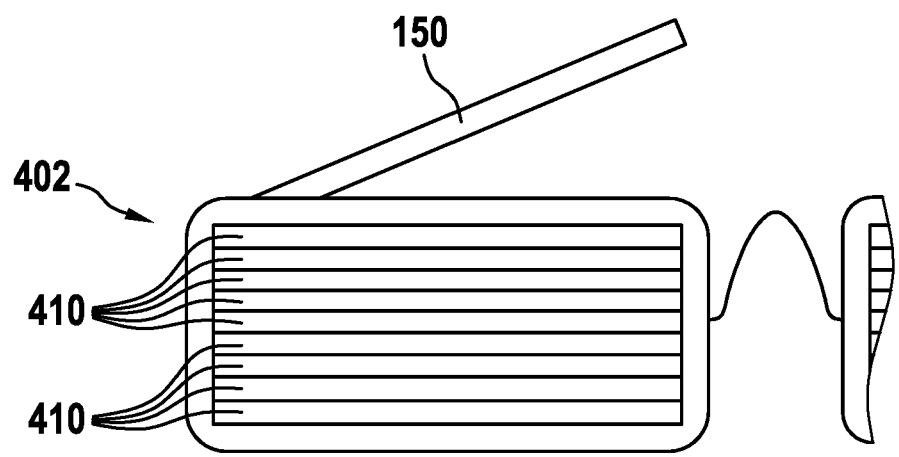
FIG. 10 shows a pair of smart glasses having an eyeglass lens according to the specific embodiment of FIGS. 8 and 9.

A further variant of this approach is shown in FIGS. 8, 9 and 10. In this connection, the eyebox regions or areas 410 extend on eyeglass lens 402 over, in each instance, an entire row length of a scanning row, as FIG. 10 illustrates. In addition, eyebox regions or areas 410 may extend over a plurality of scanning rows. All laser beams 106 within an eyebox region 410 are each projected onto a fixed position on eye 108, the so-called eyebox, as can be seen in FIG. 8, e.g., for eyebox region A, and FIG. 9, e.g., for eyebox region G.

In a high-resolution projection system having, for example, 720 rows, sufficient scanning points 110 are produced for measuring the viewing angle with a comparatively long residence time at a measuring point.

Figure 11:
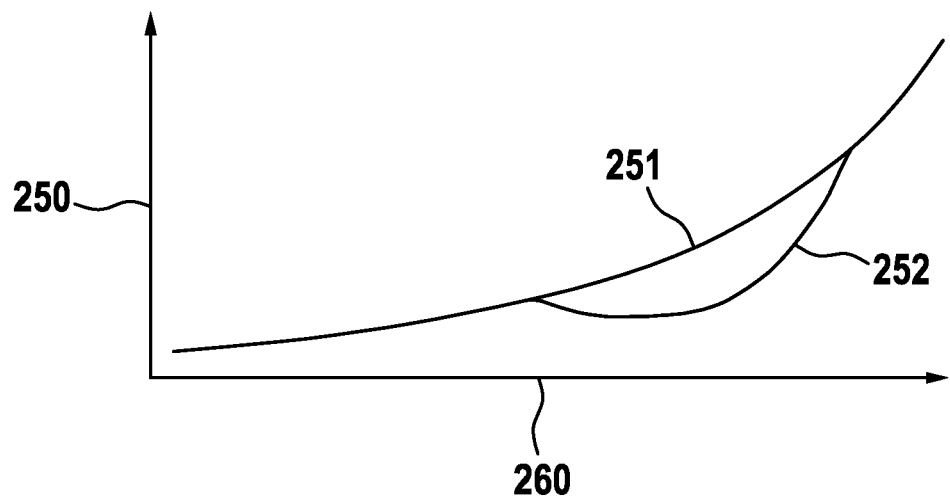
FIG. 11 shows schematic measurement data of the optical path length as a function of a horizontal scanning angle in accordance with a specific embodiment of the method of the present invention.
Figure 12:
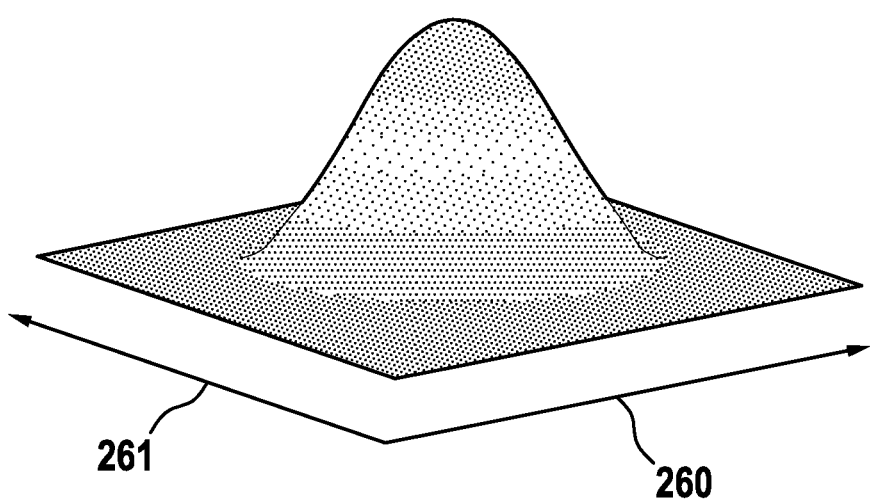
FIGS. 12 and 13 show schematic measurement results of a specific embodiment of the method of the present invention.
Figure 13:
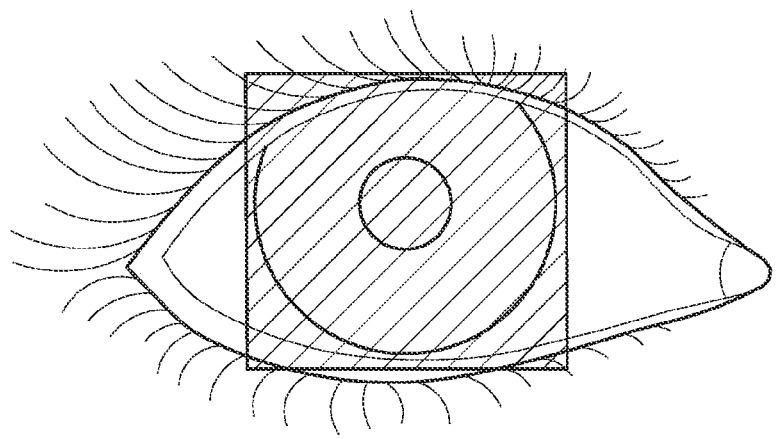

FIG. 11 shows an exemplary determination of an optical path length 250 as a function of horizontal scanning angle 260 in accordance with implementation principle 2, using an HOE functionality corresponding to FIG. 4. A contribution 251 of the reference plane of optical path length 250 describes an influence of the distance between laser 104 and deflecting element 102. Surface profile 252 of eye 108, which is presently measured as a distance, as well, is superimposed on it. Viewing direction 120 of eye 108 may be determined from surface profile 252 of eye 108. In this connection, evaluation methods may be direct parameters of the curvature, such as points of inflection, intersection points and extreme points, although so-called template matching, in which a modeling function is adapted to the measured data, may also be used. FIGS. 12 and 13 show a roughly sketched representation of the results of a measurement in accordance with implementation principle 1b.

FIG. 12 shows the reflected laser intensity plotted versus horizontal scanning angle 260 and vertical scanning angle 261. FIG. 13 shows a 2-D projection of an intensity in the coordinate system of eye 108. Using signal processing methods, the center position of pupil 118, as well as a viewing direction, may be ascertained subsequently.

Since laser 104 and the photodiode are accommodated in the same chip, the red-eye condition is automatically satisfied, which means that the laser source and the detector lie on the same axis. Consequently, the received optical power increases as soon as laser beam 106 travels through pupil 118 to the reflective retina 113. Only a little optical power is scattered back outside of pupil 118, since the shape of eye 108, that is, of the eyeball, reflects the most power away from the detection axis, that is, from viewing direction 120.

If the intensity scan is combined, e.g., to form a two-dimensional array, then, after optional filtering, the maximum or the center point of the reflection maximum may be determined, and the viewing direction may be ascertained from it.

The filtering may be a spatial kernel smoother, which produces smoothing of the signals, so that software, which seeks a maximum of the intensity distribution, does not find an outlier next to the main maximum.

Figure 14:
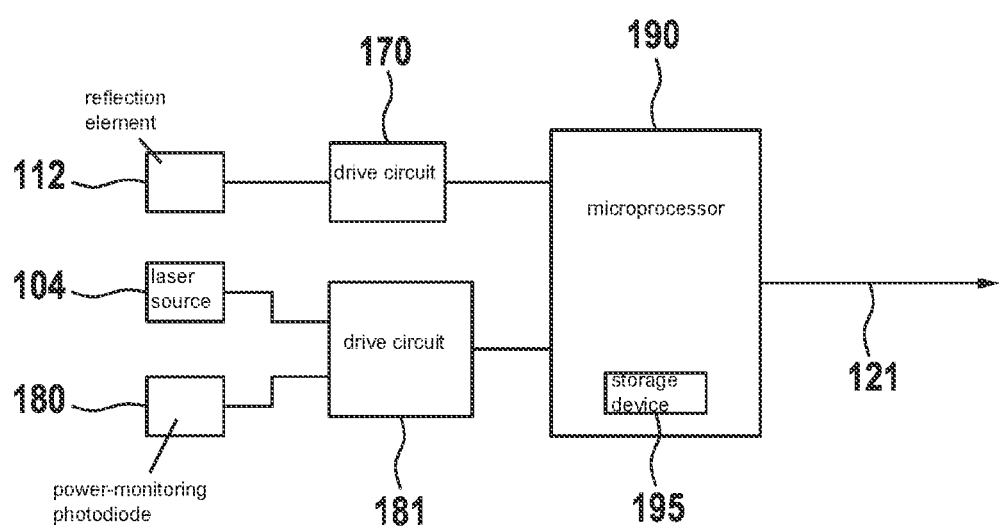
FIG. 14 shows a block diagram of a specific embodiment of a projection device in accordance with the present invention.

FIG. 14 shows a block diagram of projection device 100 for smart glasses 400. Projection device 100 includes micromirror 112 with associated drive circuit 170, an infrared laser 104, and a power-monitoring photodiode 180 having a corresponding drive circuit 181. In this case, photodiode 180 is integrated in laser 104. Additionally shown, is a microprocessor 190, that is, an electronic control unit, for executing the program code, that is, of a computer program, in order to calculate a value 121 for viewing direction 120; the microprocessor including a corresponding storage device 195 for calibration information. Calculated value 121 for viewing direction 120 may be transmitted subsequently to downstream system units.

What is claimed is:

1. A method for ascertaining a viewing direction of an eye, the method comprising the following steps:
   passing a laser beam emitted by a laser source over at least two scanning points on the eye, using a reflection element and a deflecting element; and
   using a self-mixing effect of the scanning laser beam reflected by the eye into the laser source to determine, for the at least two scanning points, an optical path length from the laser source to the at least two scanning points on a surface of the eye and/or a reflectivity of the eye at the at least two scanning points.

2. The method as recited in claim 1, wherein the viewing direction of the eye is ascertained based on different reflectivities of different parts of the eye at the at least two scanning points.

3. The method as recited in claim 1, wherein the viewing direction of the eye is ascertained, using the "red-eye effect," in that a scanning point is sought, in which an angle of incidence of the laser beam corresponds to the viewing direction of the eye.

4. The method as recited in claim 1, wherein a surface profile of the eye is ascertained, in that with the aid of the self-mixing effect, which causes modulation of the laser power while the laser beam is passed over the eye, a change in an optical path length from the laser source to a current scanning point on the surface of the eye is ascertained.

5. The method as recited in claim 1, wherein the deflecting element is a holographic optical element.

6. The method as recited in claim 1, wherein the deflecting element is positioned and configured in such a manner, that for each scanning position of the reflection element, the laser beam is deflected by the deflecting element in, in each instance, the same direction.

7. The method as recited in claim 1, wherein the deflecting element is positioned and configured in such a manner, that for each scanning position of the reflection element, there is an eye position, whose viewing direction is parallel to a propagation direction of the laser beam deflected by the deflecting element in the scanning position.

8. The method as recited in claim 1, wherein the deflecting element is positioned and configured in such a manner, that laser beams, which are deflected by the deflecting element for different scanning positions of the reflection element, are divergent.

9. The method as recited in claim 1, wherein the deflecting element is positioned and configured in such a manner, that the deflecting element has at least two different regions, and, wherein, in each instance, each region of the deflecting element deflects laser beams striking it onto a point on the eye.

10. A projection device for a pair of smart glasses, the projection device comprising:
- a light source configured to emit a laser beam;
- a deflecting element positioned or positionable on an eyeglass lens of the smart glasses, to deflect the laser beam in a direction of an eye of the user and/or to focus the laser beam; and
- a reflection element configured to reflect the laser beam onto the deflecting element;
- wherein the projection device is constructed and configured to:
  - pass the laser beam emitted by the laser source over at least two scanning points on the eye, using the reflection element and the deflecting element; and
  - use a self-mixing effect of the scanning laser beam reflected by the eye into the laser source to determine, for the at least two scanning points, an optical path length from the laser source to the at least two scanning points on a surface of the eye and/or a reflectivity of the eye at the at least two scanning points.

11. A pair of smart glasses, comprising:
an eyeglass lens; and
a projection device including a light source configured to emit a laser beam, a deflecting element configured to deflect the laser beam in a direction of an eye of the user and/or to focus the laser beam, and a reflection element configured to reflect the laser beam onto the deflecting element, wherein the projection device is constructed and configured to: pass the laser beam emitted by the laser source over at least two scanning points on the eye, using the reflection element and the deflecting element, and use a self-mixing effect of the scanning laser beam reflected by the eye into the laser source to determine, for the at least two scanning points, an optical path length from the laser source to the at least two scanning points on a surface of the eye and/or a reflectivity of the eye at the at least two scanning points;
wherein the deflecting element is situated on or in the eyeglass lens.

12. A non-transitory machine-readable storage medium on which is stored a computer program for ascertaining a viewing direction of an eye, the computer program, when executed by a computer, causing the computer to perform the following steps:
- passing a laser beam emitted by a laser source over at least two scanning points on the eye, using a reflection element and a deflecting element; and
- using a self-mixing effect of the scanning laser beam reflected by the eye into the laser source to determine, for the at least two scanning points, an optical path length from the laser source to the at least two scanning points on a surface of the eye and/or a reflectivity of the eye at the at least two scanning points.

13. An electronic control unit configured to ascertain a viewing direction of an eye, the electronic control unit configured to:
- pass a laser beam emitted by a laser source over at least two scanning points on the eye, using a reflection element and a deflecting element; and
- use a self-mixing effect of the scanning laser beam reflected by the eye into the laser source to determine, for the at least two scanning points, an optical path length from the laser source to the at least two scanning points on a surface of the eye and/or a reflectivity of the eye at the at least two scanning points.

* * * * *